United States Patent
Blanton

(10) Patent No.: US 6,419,940 B1
(45) Date of Patent: Jul. 16, 2002

(54) DENVER'S STING STOPPER

(76) Inventor: Denver Blanton, 2224 Oakwood Rd., Franklin, TN (US) 37064

( * ) Notice: Subject to any disclaimer, the term of this patent is extended or adjusted under 35 U.S.C. 154(b) by 0 days.

(21) Appl. No.: 09/928,903

(22) Filed: Aug. 14, 2001

(51) Int. Cl.$^7$ .................................................. A61K 9/00
(52) U.S. Cl. ........................ 424/401; 514/829; 514/830
(58) Field of Search ................................ 424/400, 401, 424/405, 406

(56) References Cited

U.S. PATENT DOCUMENTS

| | | | | |
|---|---|---|---|---|
| 5,753,244 A | * | 5/1998 | Reynold et al. | 424/400 |
| 6,069,169 A | * | 5/2000 | Ptchelintsev et al. | 424/70.1 |

FOREIGN PATENT DOCUMENTS

| | | | | |
|---|---|---|---|---|
| JP | 2000247893 A | * | 9/2000 | A61K/33/06 |

* cited by examiner

*Primary Examiner*—Thurman K. Page
*Assistant Examiner*—Robert M. Joynes

(57) ABSTRACT

A composition of neutralizing the venom of bees, wasps, hornets, yellow jackets and other sting any hymenoptera insects.

The composition comprises a proteclytic enzyme with a carrier suitable for topical application to the skin. In a preferred embodiment the enzyme triethanolamine and the composition also includes anhydrous aluminum silicate to increase the penetrating ability of the composition and methyl red as an indicator solutior.

7 Claims, No Drawings

DENVER'S STING STOPPER

BACKGROUND OF THE INVENTION

The present invention relates to a topical compound that will neutralize the pain and reduce the swelling of Hymenoptera and other stinging insects. There are various topical compounds to reduce the pain of stings using Galic, Papain, Bromelains and other Protealytic enzymes for relieving the symptoms to stings but they only relieve the sting, they don't neutralize. The invention alleviates the pain from the sting and reduces the swelling in minutes instead of just relieving the pain.

The invention was discovered by the need for the relief of a sting and by knowing the relief given by the aforementioned compounds and I discovered the invention by the insight I had of other solutions. Since the invention advances the relief over all other compounds used to date. It will benefit anyone needing to alleviate the results from stings.

SUMMARY OF THE INVENTION

The invention is based on the discovery that triethanolamine in combination with anhydrous aluminum silicate and methyl red are effective in eliminating the pain and swelling when toxicants are introduced into the epidermis and thereby assists in any allergic reaction to stings.

The invention, a composition mentioned above, eliminates the sting and pain and swelling of an insect when applied topically to the sting area.

The preparation of the compound is as follows and the amounts are by weight.

EXAMPLE

60% Daltogen (Sigma Chemical Co), 38% Anhydrous Aluminum Silicate (Burgess Company) and 2% Methyl Red (Integra Chemical Co) each chemical added slowly and mixed thoroughly.

Although the present invention is described with preferred embodiments, the invention is not limited to these but instead includes all those embodiments within the spirit and scope of the appended claim. This compound is applied directly to the sting area and massaged into affected area.

DESCRIPTION OF INVENTION

The present invention relates to a topical compound that will neutralize the pain and reduce the swelling of Hymenoptera and other stinging insects.

There are various topical compounds to reduce the pain of stings using Gallic Acid, Papainase, bromelains and other proteolytic enzymes for relieving symptoms relating to episiotomy.

All other compounds relieve the symptoms of stings but the invention alleviates the symptoms of stings in minutes.

The invention was discovered by the need for relief and by knowing the relief given by the aforementioned compounds I started trying to find a better compound and the invention is the result.

Since the invention advances the relief over all other compounds used to date, it will benefit anyone needing to alleviate the results from stings.

DRAWINGS

Not Applicable

What is claimed is:

1. A composition for eliminating the pain of a sting in seconds and the swelling in minutes of a sting from a Hymenoptera and other stinging insects consisting essentially of a sting neutralizing amount of triethanolamine, anhydrous aluminum silicate, methyl red and a carrier suitable for topical application to the skin.

2. The composition of claim 1 where the carrier is water.

3. The composition of claim 1 where the anhydrous aluminum silicate is present at 30 to 40% based on weight to the triethanolamine.

4. The composition of claim 1 where the methyl red is present at 0.5 to 2%, based on the weight of the triethanolamine and anhydrous aluminum silicate.

5. A method of neutralizing the sting venom of Hymenoptera and other stinging insects by applying topically to the skin, a composition consisting of a sting venom neutralizer of triethanolamine, anhydrous aluminum silicate and methyl red suitable for topical application to the skin.

6. The method of claim 5 wherein the anhydrous aluminum silicate is present at 30 to 40% based on the weight of the triethanolamine.

7. The method of claim 5 where the methyl red is present at 0.5 to 2% based on the weight of the triethanolamine and anhydrous aluminum silicate.

\* \* \* \* \*